United States Patent [19]

Kappas et al.

[11] Patent Number: 5,061,477
[45] Date of Patent: Oct. 29, 1991

[54] USE OF COBALT TO ENHANCE URINARY COPPER EXCRETION

[75] Inventors: Attallah Kappas; Daniel W. Rosenberg, both of New York, N.Y.

[73] Assignee: The Rockefeller University, New York, N.Y.

[21] Appl. No.: 336,681

[22] Filed: Apr. 11, 1989

[51] Int. Cl.$^5$ .................... A61K 49/00; A61K 33/26
[52] U.S. Cl. ........................................ 424/10; 424/646
[58] Field of Search ........................... 424/646, 10

[56] References Cited

U.S. PATENT DOCUMENTS 2,968,653  1/1961  Klotz ................................. 424/646

FOREIGN PATENT DOCUMENTS 2089660  6/1982  United Kingdom ............... 424/646

OTHER PUBLICATIONS

The Merck Manual, 14th ed., pp. 913–915 (1982).

Primary Examiner—Stanley J. Friedman
Assistant Examiner—Raymond J. Henley, III
Attorney, Agent, or Firm—Wyatt, Gerber, Burke and Badie

[57] ABSTRACT

A method for reducing the copper burden in mammals without zincuresis utilizing cobalt salts or chelates.

13 Claims, 4 Drawing Sheets

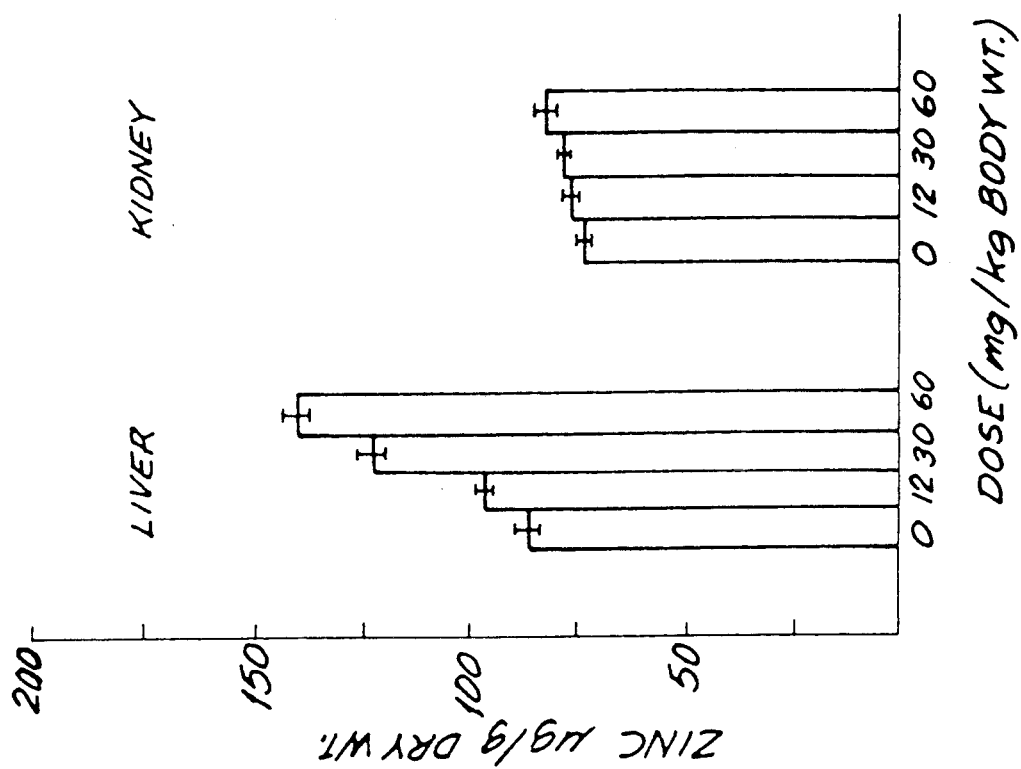
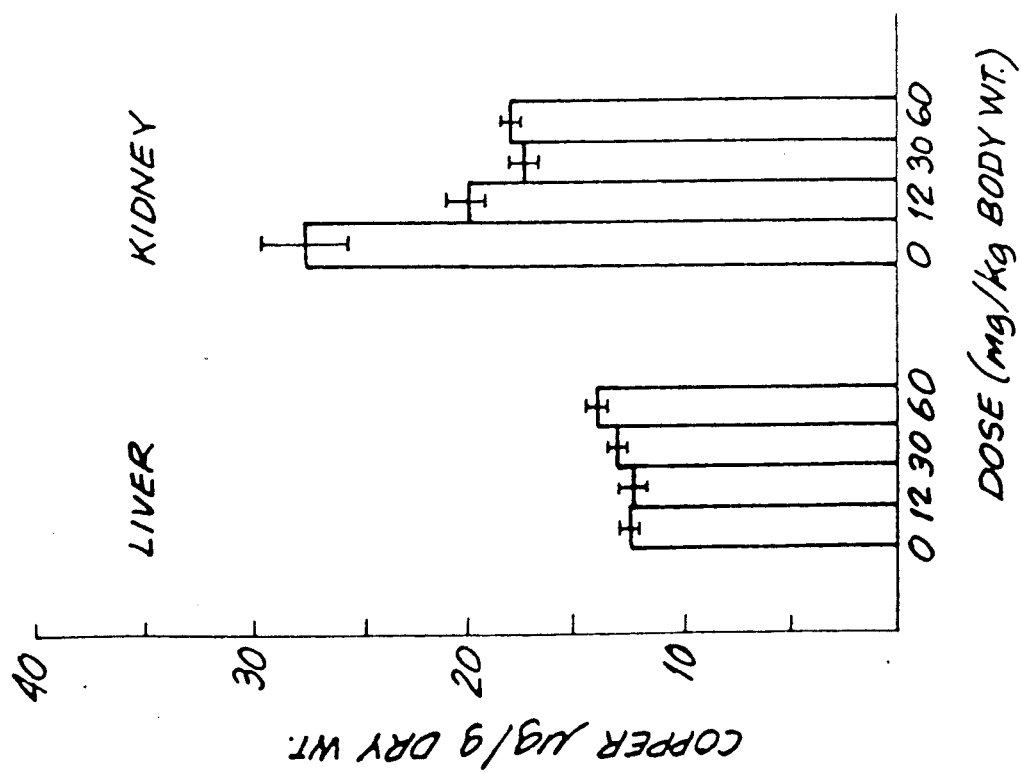

5,061,477

USE OF COBALT TO ENHANCE URINARY COPPER EXCRETION

FIELD OF THE INVENTION

This invention relates generally to the alteration of copper and zinc metabolism in mammals, including humans, and is particularly related to the use of cobalt compounds, including cobalt salts and cobalt chelates in such method. More specifically, the present invention relates to the treatment of mammals with cobalt ions from non-toxic inorganic cobalt salts or chelates in order to decrease their copper burden without zincuresis (loss of zinc).

BACKGROUND OF THE INVENTION

The metabolic significance of copper in mammals, which include humans, has long been recognized. An increased number of human disorders have been associated with copper deficiency similar to disorders observed with copper deficiency in animals. These include anemia, abnormal bone formation, reproductive failure, heart failure, bone abnormalities associated with spontaneous fracture and arterial and cardiac aneurysm.

While it is of paramount importance to maintain adequate copper levels through appropriate dietary intake, it is equally significant to avoid an excessive copper burden that can result in copper poisoning or copper toxicity. The clinical manifestations of copper poisoning in mammals have been known and well described in various publications. These manifestations, which are similar to other metal poisoning, include a metallic taste in the mouth, nausea, vomiting, diarrhea and host of other disorders.

Copper toxicity in mammals may arise due to specific genetic defects, environmental exposure and increased body burden associated with aging. The most notable example of a genetic metabolic defect in human is seen in patients with Wilson's disease. In such patients, copper accumulates in the liver, renal tubules, cornea, brain and other organs causing damage to these structures.

Toxic levels of copper have also been noted in cases of exposure. Accidental ingestion of copper sulfate is not uncommon in children. Some of the more common cases of copper toxicity result from drinking water, foods cooked in copper vessels, soft drinks served from defective equipment and alcoholic beverages brewed or stored in copper lined containers. Industrial exposure to copper, such as exposure to copper oxide fumes, is also common although such exposures result more in dermatologic and respiratory symptoms. Age-related copper toxicity has also been observed due to an accumulation in tissue levels of copper.

Regardless of whether copper toxicity is due to a genetic defect, results from environmental or industrial exposure, or comes about because of aging tissues, its adverse and toxicological symptoms can only be eliminated if the host is capable of systematically disposing of the excess copper.

Heretofore, copper excretion from animals was promoted by treatment with penicillamine, a chelating agent. However, as will hereinafter be discussed, while treatment of animals with penicillamine results in enhanced copper excretion from the system, the administration of this therapeutic agent also results in significant zincuresis as well as losses of other essential trace elements from the system which disturbs the metabolic operation of the body. Loss of zinc is a very serious matter, since this element is involved in more than 125 enzymatic processes in the mammalian body.

In view of these disadvantages of treatment with penicillamine, investigators have directed their attentions to other forms of therapy for diseases resulting from excess copper levels in the system and its attendant physiological toxicity problems. In order to make-up for the zincuresis, some have prescribed oral administration of zinc in dosages designed to alleviate the zincuresis effect of penicillamine therapy. So far as is known, there is no treatment method presently available for reducing the copper level in mammals without concomitant reduction or depletion of zinc from the system.

Accordingly, it is an object of the present invention to provide a method of treatment of mammals whereby their copper burden is reduced without adverse metabolic or other toxic effects.

It is a further object of this invention to provide a method of treatment of mammals to reduce their copper level without any clinically significant zincuresis.

It is still a further object of this invention to administer non-toxic inorganic cobalt compounds, including cobalt salts or cobalt chelates to mammals in order to reduce their copper level to chemically acceptable and non-toxic levels.

It is yet another object of this invention to treat mammals with cobalt chloride or dicobalt ethylenediaminetetraacetic acid ($CO_2$ EDTA) to reduce their copper level without simultaneously reducing their zinc level or depleting from their systems other desirable trace metals.

The foregoing and other features and advantages of the present invention will become more evident from the ensuing detailed description and the accompanying figures.

SUMMARY OF THE INVENTION

Treatment of mammals with cobalt compounds, notably cobalt chloride or $CO_2$ EDTA significantly reduces the copper burden of mammals without simultaneous zincuresis. The cobalt compound will normally be administered parenterally. The presently preferred route is subcutaneous. This treatment results in a significant increase in urinary copper excretion as well as a reduction of the copper level in plasma, without an associated zincuresis. In contrast, treatment with penicillamine, the only known therapeutic agent for reduction of copper burden in mammals, produce various undesirable adverse effects, including a significant zincuresis.

BRIEF DESCRIPTION OF THE DRAWINGS

FIG. 2A is a series of graphs illustrating the effect of cobalt chloride at three dose levels on the tissue copper level after 24 hours;

FIG. 2B is similar to FIG. 2A but illustrates the effect on zinc;

DETAILED DESCRIPTION OF THE INVENTION

Figure 1B:
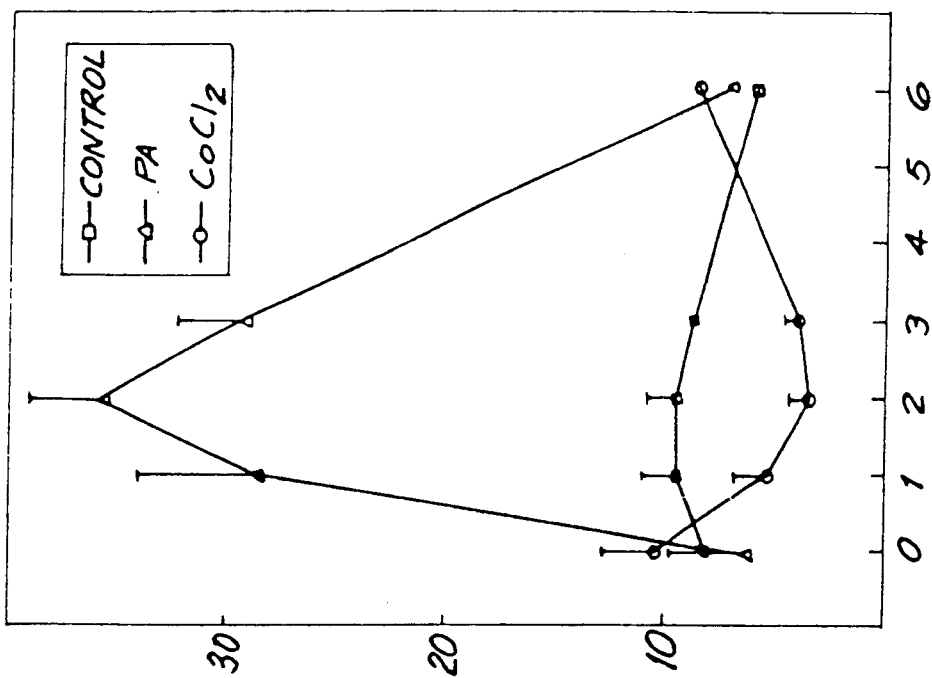
FIG. 1B is similar to FIG. 1A but illustrates the zinc output in urine.

It has been surprisingly discovered that when mammals are treated with cobalt ions, typically as cobalt chloride, or $Co_2$ EDTA, their copper burden is reduced without concomitant reduction of zinc levels or (loss of other essential trace elements). This discovery was surprising because the only known therapeutic method of reducing the copper level was treatment with D-penicillamine which, however, was always accompanied by considerable zincuresis and even loss of other essential trace elements.

Although cobalt chloride has been known for years and has been used in the treatment of cyanide poisoning through the chelating action of the cobalt ion to form a stable metal complex with cyanide, the use of cobalt has not received much clinical support due to the toxicity of cobalt ion when administered at high doses in some forms. Therefore, it was surprising to find that when cobalt chloride is administered to mammals in accordance with this invention, the copper level was significantly reduced without zincuresis or loss of other essential trace metals. This was particularly surprising because of the highly complex and unpredictable nature of the interrelationships among metals and the effect of administration of one metal in animals. Although the administration of one element to animals can often affect the metabolism and tissue distribution of other metals, these effects are not predictable. It has been discovered, in accordance with this invention, that administration of cobalt chloride to mammals accelerates urinary copper excretion. As discussed and illustrated below, the administration of cobalt chloride to Sprague-Dawley rats lowers tissue copper levels in the kidney; increases zinc levels in liver, and significantly enhances the urinary excretion of copper without concomitant zincuresis. This biological activity of cobalt is new and unexpected in view of the state of the art and the unpredictable interrelationship of effects of metals on biological activities.

The highly beneficial and surprising results of the method of this invention will now be described in the following experiments, using cobalt chloride as the source of cobalt ion. However, it must be emphasized at the outset that the experimental procedure hereinafter described is illustrative and should not be interpreted so as to limit the scope of the present invention. In particular, while cobalt chloride constitutes the present therapeutic agent of choice for the purpose of this invention, other sources of cobalt ion may be employed. Thus, the source of cobalt ions may include other non-toxic cobalt salts, preferably inorganic cobalt salts and cobalt chelates, as will hereinafter be described.

EXPERIMENTAL PROCEDURES

A. Materials

The test subjects were male Sprague-Dawley rats (150–300 g.) acquired from Taconic Farm in Germantown, N.Y.

Cobaltous chloride ($CoCl_2 6H_2O$) was obtained from Mallinkdrodt Chemical Co., St. Louis, Mo.

Inorganic metal standards were purchased from either VWR, South Plainfield, N.J. or the Ventrol Corp., Danvers, Mass.

Untrex grade nitric acid, obtained from J. T. Baker Chemical Co., Phillipsburg, N.J. was used for sample digestions and preparation of standards.

Penicillamine was obtained from Aldrich Chemical Company, Inc., Milwaukee, Wis.

Gel Filtration calibration standards were purchased from Pharmacia Fine Chemicals, Piscataway, N.J.

All other reagents used in these experiments were of high commercial grade and were acquired from Sigma Chemical Co., St. Louis, Mo.

Distilled water was further purified in a Millipore deionizer consisting of Mill-Q system and the purified water (dd $H_2O$) was used in all experiments.

Nalgene metabolic cages for 150–300 g. rats were purchased from Sybron/Nalge, Rochester, N.Y.

All glassware, metabolic cages and material that would come into contact with the samples for subsequent trace metal analysis were washed with detergent, soaked overnight in dilute (10%) reagent grade nitric acid, and rinsed first in distilled water and then rinsed repeatedly with deionized water.

B. Treatment of Animals

The test rats were maintained on Purina Rodent Chow 5001 (St. Louis, Mo.) and were allowed to acclimatize before placing them in the metabolic cages. Urine samples were collected at 24 hour intervals throughout the experiment. Cobalt chloride was dissolved in saline and injected into the rats subcutaneously at a single dose of 12, 30 or 60 mg/kg body weight (b.w.). Penicillamine was dissolved in a separate saline solution and administered to the rats by gavage in 1, 2 or 3 daily doses of 50 mg/kg b.w. using a Perfektum (New Hyde Park, N.Y.) stainless steel 18 gauge animal feeding needle. This dosage compares with the clinically proven effective dosage of this drug.

In a separate experiment to compare different routes of administration of the drug to the rats, groups of rats were injected daily with cobalt chloride at a dose of 12 mg/kg b.w. subcutaneously or intraperitoneally for 3 days. Throughout all experiments, the rats were allowed free access to food and distilled water until they were sacrificed by decapitation.

C. Tissue Preparation

After the animals were sacrificed, they were exhaustively perfused in situ with ice-cold 0.9% sodium chloride solution through the left ventricle. Their livers and kidneys were removed, blotted dry and the wet tissue weight was recorded. The entire left kidney and a 1 gram portion of finely minced liver were then dried to a constant weight on a Teflon watch glass at 100°–130° C. The dried tissue was thereafter placed in a 14 ml. sterile polypropylene screw scrap test tube (Sarstedt, Inc., Princeton, N.J.). Ultrex nitric acid (75% v/v) was then carefully added to the samples in a minimum volume to effect complete sample dissolution, typically at a ratio of 1:10 to 1:20 (v/w) and the samples were then maintained at room temperature for 1 hour to initiate the digestion process and avoid excessive frothing. The samples were heated in a water bath maintained at 60°-80°C. until all tissue had dissolved. The resulting solutions were diluted to a final volume of 5 or 10 ml with double distilled H2O and filtered through a 0.45 MM millexMA filter unit (Millipore Corp., Bedford, Mass.). Immediately after their collection, the urine samples were acidified with nitric acid (1% v/v) and centrifuged at 600 xg for 10 minutes to remove undesirable sediments.

D. Metal Analysis

All trace element analyses were performed on a Zeeman/500 atomic absorption spectrophotometer equipped with an HGA-500 graphite furnace obtained from Perkin-Elmer Corp., Norwalk, Conn., using a deuterium lamp for background correction in the flame mode, and Zeeman background correction for all graphite furnace determinations. Copper and zinc levels were measured in tissue acid digests and column eluates were measured in air-acetylene flame using a 10 CM burner head and a flow spoiler, at wavelengths of 324.8 nm and 213.9 nm, respectively. The graphite furnace utilized L'vov platform with appropriate wavelength and instrumental operating conditions as optimized in the laboratory for individual metal analyses. Recovery experiments were routinely carried out in each tissue to characterize the behavior of the particular metal within the give matrix. In case of interference occurring in analysis, the metal concentration was determined from a standard curve made up in the given matrix under study (method of additions calbration).

E. Plasma copper and zinc levels and enzyme determinations

Blood samples were collected by repetitive bleeding of the tail vein in hepatinized microhematocrit capillary tubes (Sherwood Medical Ind., Td. Louis, Mo.). The tubes were spun in an Autocrit II to separate plasma. For zinc and copper determinations, 10 ul plasma samples were pipetted into polystyrene sample cups (Sarstedt, Inc., Princeton, N.J.) and diluted 100-fold with deionized water. A final concentration of 0.1% triton X-100 was routinely included in all samples and standards as a pipetting aid. Plasma, copper and zinc levels were then determined by graphite furnace atomic absorption spectroscopy.

F. Subcellular fractionation and gel filtration

Livers were exhaustively perfused in situ with ice-cold 0.9% NaCl and homogenized in 3 volumes of potassium phosphate buffer (0.1M, pH 7.4) containing sucrose (0.25M). The homogenates were centrifuged at 900xg for 20 minutes. The resulting supernatant fraction was centrifuged at 105,000xg for 60 minutes in a Beckman L5-50 ultracentrifuge. The 105,000xg (cytosolic) fraction obtained from liver generally contained between 20-25 mg protein/ml. 2.5 ml aliquots of the liver 105,000xg supernatants were then applied to a Sephadex G-75 column (2.6×54 cm) equilibrated with 0.01M potassium phosphate buffer (pH 7.4) and maintained at 4° C. The column was eluted at a flow rate of 15 ml/hr with a fraction size of 5 ml. Fractions were monitored for protein at 280 nm, and then analyzed for zinc content by flame atomic absorption spectroscopy as described above.

All data were analyzed by either Student's t-test or Dunnett's multiple comparison of treatments against a single control, and p values less than 0.05 were regarded as statistically significant.

The results of the foregoing experiments are discussed below with reference to the figures.

A. Urinary excretion of copper and zinc

Figure 1A:
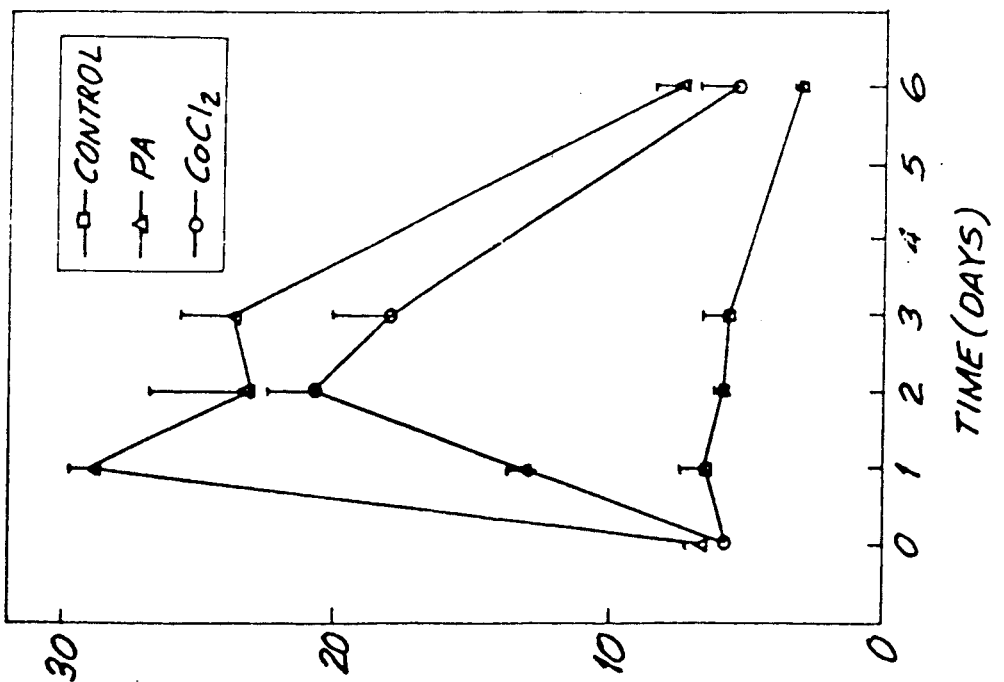
FIG. 1A is a series of three graphs illustrating the copper output in urine following treatment with cobalt chloride and comparing it with copper output in urine following treatment with D-penicillamine and controls.

The urinary excretion of copper and zinc are shown in FIGS. 1A and 1B, respectively. In each figure, the results show urinary excretion following treatment with penicillamine (50 mg/kg b.w. per day, administered orally) in three daily doses; treatment with cobalt (60 mg/kg b.w., administered subcutaneously) in a single dose measured over 6 days at time intervals shown in FIGS. 1A and 1B.

Referring specifically to FIG. 1A, it is noted that the copper output, expressed in ug/24 hrs., in urine from saline-treated animals ranged from $3.07 \pm 0.33$ to $6.34 \pm 1.01$ ug/24 hrs. throughout the 6 day period. Treatment with penicillamine in 3 doses rapidly increased urine excretion approximately 6-fold within the first 24 hours, while treatment with a single dose of cobalt chloride resulted in 4-fold urinary excretion after an initial 24 hour lay period.

In the same animals, and referring to FIG. 1B, urinary zinc output, also expressed in ug/24 hrs., for the control animals varied over the 6 day experimental period from $5.34 \pm 0.26$ to $9.60 \pm 1.22$ ug/24 hrs. After treatment with 3 daily doses of penicillamine, the zinc level in urine of the test animals markedly increased within 24 hours after treatment. As seen from FIG. 1B, this increase corresponded to about 4-fold above the controls after 2 days of treatment. The zincuresis subsided upon termination of treatment with penicillamine, and after 5 days the urine zinc levels returned to normal. In contrast to treatment with penicillamine, a single dose of cobalt chloride administered to animals resulted in 20-30% decrease in urinary zinc levels compared to controls. This reduced zinc level was maintained for at least 3 days after treatment with cobalt chloride before finally reverting to normal levels after 6 days.

In addition to determining the effect of a single dose treatment as hereinbefore described, 12 mg/kg of cobalt chloride were injected in the animals subcutaneously in three daily doses. The treatment was similar to the penicillamine treatment described in the foregoing experiments. The results are shown in Table I below.

TABLE I

| Route of Administration | Treatment | Cumulative urinary output (0-72 hours) | |
|---|---|---|---|
| | | Copper (ug) | Zinc (ug) |
| SUB-CUTANEOUS | Saline | 27.51 ± 0.19 | 31.52 ± 3.48 |
| | Cobalt chloride | 75.07 ± 3.35[a] | 20.58 ± 0.21[b] |
| INTRA-PERITONEAL | Saline | 20.88 ± 2.44 | 22.21 ± 3.30 |
| | Cobalt Chloride | 51.15 ± 6.54[c] | 12.69 ± 2.42 |

[a]These values were significantly different from the controls treated with saline alone (p < 0.01, Student's t-test)
[b]p < 0.05
[c]p < 0.02

As shown in Table 1, subcutaneous treatment of the animals with three smaller doses at 24 hour intervals resulted in 3-fold increase in urinary copper excretion during the 3-day period. In the meantime, zinc output was reduced by approximately 35%.

As further shown in Table I, intraperitoneal adminsitration of cobalt to the animals was effective in increasing the urinary copper excretion by about 2.5-fold while reducing the zinc output by approximately 40%.

It will be seen therefore that treatment of mammals with cobalt sale resulted in significant increase in urinary copper excretion without zincuresis.

B. Effect of Treatment with cobalt chloride or D-penicillamine on tissue, copper zinc levels Table II below shows the tissue levels of copper and zinc in liver and kidney after 1 and 3 days resulting from either a single dose treatment with cobalt chloride (60 mg/kg b.w.) or daily doses with penicillamine (50 mg/kg b.w. per day).

TABLE II

| Treatment | Liver | Kidney | Liver | Kidney |
|---|---|---|---|---|
| Day 1 | | | | |
| Controls | 12.3 ± 0.1 | 21.4 ± 1.8 | 96.1 ± 7.3 | 72.5 ± 0.3 |
| Cobalt chloride (60 mg/kg × 3) | 13.8 ± 0.6 | 15.8 ± 0.7 | 129.1 ± 5.7$^a$ | 75.7 ± 3.0 |
| Day 3 | | | | |
| Controls | 10.4 ± 0.1 | 31.1 ± 2.3 | 68.8 ± 1.5 | 64.7 ± 1.5 |
| Cobalt chloride | 10.7 ± 0.5 | 20.1 ± 14$^a$ | 90.4 ± 2.8$^a$ | 70.4 ± 2.6 |
| D-Penicillamine | 10.8 ± 0.1 | 21.9 ± 1.3$^a$ | 76.5 ± 1.7$^a$ | 62.7 ± 2.9 |

$^a$These values were significantly different from the controls treated with saline alone ($p < 0.05$, Dunnett's multiple comparison).

As shown in Table II, treatment with cobalt chloride resulted in about 25% reduction of kidney copper level in one day while treatment with penicillamine resulted in approximately 15% increase in renal copper level after the same time period. However, three doses of penicillamine were required over 72 hour period in order to reduce the renal copper level to about 35%.

As far as the hepatic copper level is concerned, no differences were noted after treatment with cobalt chloride for one day or after 3 days treatment with penicillamine. However, after six days of treatment with a single dose of cobalt chloride or repeated treatments with penicillamine, the hepatic copper level was reduced by approximately 20%. Also, after one and three days treatment, the hepatic zinc level was elevated by approximately 30-35% when using cobalt chloride but no significant change in zinc level was detected either in the liver or kidney from penicillamine treatment.

C. Dose-related effects of treatment with cobalt chloride on copper and zinc levels of liver and kidney The results of treatment of the animals with various doses of cobalt chloride are shown in FIG. 2A and 2B. As shown in FIG. 2A, after 24 hours of treatment the single dose of cobalt chloride 912 mg/kg b.w.) produced approximately 30% reduction in renal copper level. However, this treatment had no effect on hepatic copper level. Treatment with cobalt chloride, however, resulted din an increase in hepatic zinc levels after 24 hours, as shown in FIG. 2B. As shown in this figure, the administration of 12 mg/kg b.w. of cobalt chloride to animals resulted in an approximately 10% increase in hepatic zinc levels, and further increasing doses, i.e., 30 and 60 mg/kg b.w. increased the hepatic zinc content to as high as 160% of controls. However, even the highest dose of cobalt chloride resulted din only about 1 10% increase, which is not statistically significant.

Figure 3A:
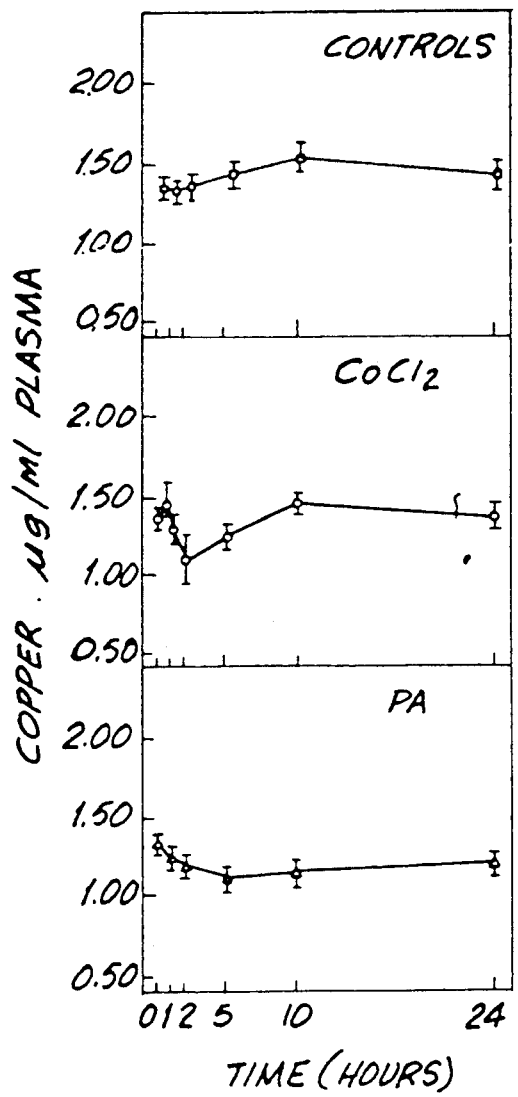
FIG. 3A is a series of graphs illustrating copper plasma levels in animals treated with cobalt chloride and comparing it with copper plasma levels in animals treated with D-penicillamine and with untreated controls.
Figure 3B:
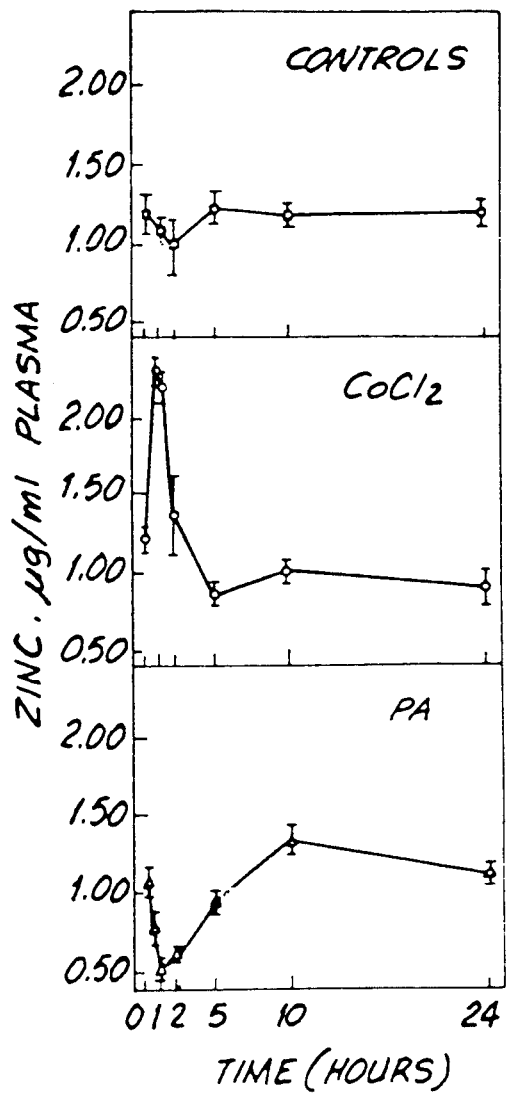
FIG. 3B is similar to FIG. 3A but illustrates the zinc levels in plasma.

D. Effect of treatment with cobalt chloride and D-penicillamine on the copper and zinc levels in plasma The results of treatment with a single dose of either cobalt chloride (60 mg/kg b.w.) or penicillamine (50 mg/kg b.w.) on the copper and zinc levels in the plasma are shown in FIGS. 3A and 3B. Thus, as shown in FIG. 3A, only treatment with cobalt chloride produced approximately a 20% reduction in plasma copper levels, which gradually returned to normal in 10 hours.

The plasma zinc level (FIG. 3B) was elevated approximately 2.5-fold within 30-60 minutes after treatment with cobalt, however, this increase was transient and the zinc level returned to its original level after about 3-4 hours. The zinc level in controls, after a small decline over the first 8 hours, remained relatively constant.

In contrast, treatment with penicillamine produced a rapid decline of about 50% in the plasma zinc level. This zinc level reached its minimum after about 1 hour, thereafter rising to its initial level over the next several hours.

Figure 4:
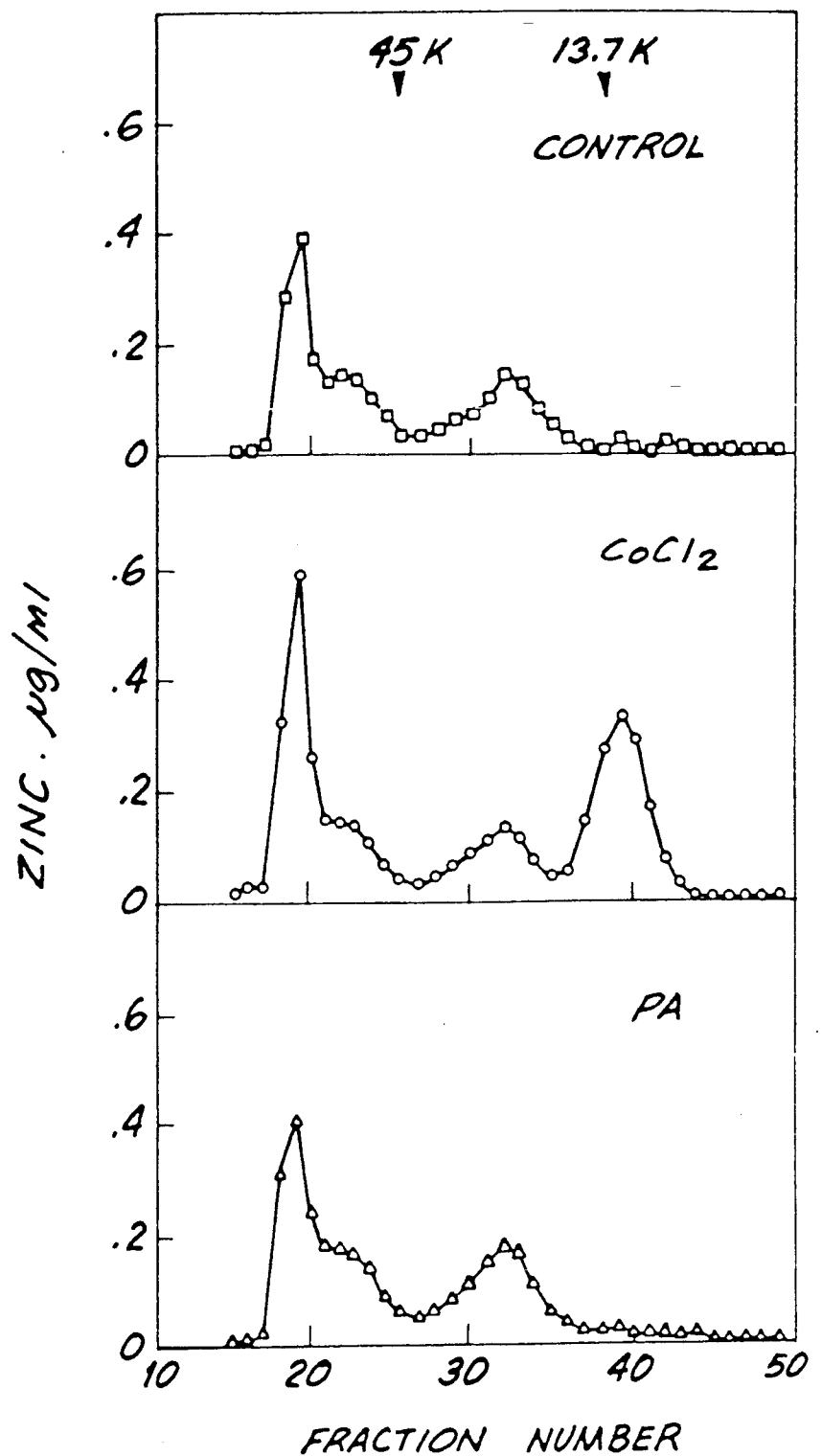
FIG. 4 is a series of three graphs representing the zinc elution profile of liver cytosols on a Sephadex G-75 column following treatment with either cobalt chloride or D-penicillamine and a third graph for untreated controls.

E. Effect of treatment with cobalt chloride and D-penicillamine on intra cellular binding of hepatic zinc Liver 105,000 xg cytosol prepared from animals receiving a single dose of cobalt (60 mg/kg b.w.) or D-penicillamine (50 mg/kg b.w.) was fractionated by gel filtration chromatography, and its zinc content was measured as described in the foregoing experiments. The chromatographic profiles of liver cytosolic zinc eluting from a Sephadex G-75 column are shown in FIG. 4 for controls, cobalt chloride treatment and treatment with penicillamine. Referring to the top graph in FIG. 4, it is seen that, in the controls, zinc eluted in three major peaks. Treatment with a single dose of penicillamine resulted in a zinc elution pattern that was virtually indistinguishable from the controls, as shown in the lowest graph in FIG. 4. In contrast, however, treatment with cobalt chloride resulted in zinc elution in three major peaks: a large molecular weight fraction corresponding to the void volume, a peak corresponding to approximately 63,000 molecular weight and a smaller peak corresponding to 30,000 molecular weight.

The foregoing description and illustrative experiments demonstrate the clinical efficency of treatment of mammals with cobalt chloride to reduce their copper burden without zincuresis. This is to be contrasted with treatment with penicillamine which results in transitory elevation in urinary copper secretion, requiring daily treatment to sustain this cupriuresis. However, and significantly, treatment with penicillamine is accompanied by considerable loss of zinc, which is one of the major adverse side-effects of penicillamine therapy. Thus, while cobalt is equally as effective as penicillamine in producing cupriuresis, treatment with cobalt chloride does not produce the deleterious zincuresis associated with penicillamine.

While the foregoing experiments were described using cobalt chloride as the therapeutic agent, other cobalt salts such as cobalt sulfate, cobalt phosphate, cobalt succinate and cobalt gluconate can also be used with efficacious results. Similarly, $CO_2$ EDTA and other cobalt chelates can also be used.

The optional dosages and regimens for a given mammalian host will obviously vary, taking into account several factors including age, weight, sex, diet, route of administration, rate of excretion, condition of the host and the degree of copper toxicity. In general, however, the dosage must be sufficient to reduce the copper burden to a non-toxic level.

Suitable compositions for use in the practice of this invention can be prepared in accordance with standard pharmaceutical procedures using the usual excepients such as 0.9% saline or glucose. Such compositions may also contain flavoring agents, preservatives, antioxidants and other standard component, together with an effective amount of the selected cobalt compound.

What is claimed is:

1. A method of reducing the level of copper in a mammal in need thereof which comprises administering to said mammal an effective copper-reducing amount of cobalt ions; wherein said mammal has toxic copper levels and does not suffer from anemia.

2. The method as in claim 1 wherein said cobalt ions are administered parenterally.

3. The method as in claim 1 wherein said cobalt ions are administered subcutaneously.

4. The method as in claim 1 wherein the source of said cobalt ions is an inorganic cobalt salt or a cobalt chelate.

5. The method as in claim 2 wherein the source of said cobalt ions is an inorganic cobalt salt or a cobalt chelate.

6. The method as in claim 3 wherein the source of said cobalt ions is an inorganic cobalt salt or a cobalt chelate.

7. The method as in claim 4 wherein said cobalt salt is cobalt chloride.

8. The method as in claim 5 wherein said cobalt salt is cobalt chloride.

9. The method as in claim 6 wherein said cobalt salt is cobalt chloride.

10. The method as in claim 4 wherein said cobalt chelate is cobalt ethylenediaminetetraacetic acid.

11. The method as in claim 5 wherein said cobalt chelate is cobalt ethylenediaminetetraacetic acid.

12. The method as in claim 6 wherein said cobalt chelate is cobalt ethylenediaminetetraacetic acid.

13. The method as in claim 1, 2, 3, 4, 5, 6, 7, 8, 9, 10, 11 or 12 wherein said mammal is a human.

* * * * *